(12) United States Patent
Danielsson et al.

(10) Patent No.: US 10,048,390 B2
(45) Date of Patent: Aug. 14, 2018

(54) DETECTOR IMPLEMENTATIONS FOR X-RAY DETECTORS

(71) Applicant: Prismatic Sensors AB, Stockholm (SE)

(72) Inventors: Mats Danielsson, Taby (SE); Mats Persson, Vasterhaninge (SE); Martin Sjolin, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 15/594,879

(22) Filed: May 15, 2017

(65) Prior Publication Data

US 2018/0045838 A1    Feb. 15, 2018

Related U.S. Application Data

(60) Provisional application No. 62/373,413, filed on Aug. 11, 2016.

(51) Int. Cl.
| | | |
|---|---|---|
| *G01T 1/24* | (2006.01) | |
| *A61B 6/03* | (2006.01) | |
| *G01N 23/04* | (2018.01) | |
| *A61B 6/00* | (2006.01) | |
| *G01N 23/046* | (2018.01) | |

(52) U.S. Cl.
CPC .............. *G01T 1/243* (2013.01); *A61B 6/032* (2013.01); *A61B 6/4233* (2013.01); *A61B 6/4266* (2013.01); *G01N 23/046* (2013.01); *G01N 2223/419* (2013.01)

(58) Field of Classification Search
CPC ..................................................... G01T 1/243
See application file for complete search history.

(56) References Cited

U.S. PATENT DOCUMENTS

| | | | |
|---|---|---|---|
| 8,183,535 B2 | 5/2012 | Danielsson et al. | |
| 2004/0000630 A1* | 1/2004 | Spartiotis | A61B 6/14 250/208.1 |
| 2010/0204942 A1* | 8/2010 | Danielsson | G01T 1/242 702/85 |
| 2010/0270462 A1* | 10/2010 | Nelson | G01T 1/2018 250/252.1 |
| 2012/0093280 A1 | 4/2012 | Konno et al. | |
| 2012/0106696 A1 | 5/2012 | Dafni | |
| 2012/0153163 A1* | 6/2012 | Levene | G01T 1/2018 250/361 R |
| 2013/0134316 A1* | 5/2013 | Nakatsugawa | G01T 1/202 250/366 |
| 2013/0266114 A1 | 10/2013 | Chen et al. | |
| 2013/0320222 A1 | 12/2013 | Abenaim et al. | |

(Continued)

OTHER PUBLICATIONS

Wang, A, et al., "Effect of Frequency Content and Spatial Location of Raw Data Errors on CT Images," Proc. of SPIE, vol. 6913, 2008, pp. 691334-1-691334-8.

(Continued)

*Primary Examiner* — David Porta
*Assistant Examiner* — Jeremy S Valentiner
(74) *Attorney, Agent, or Firm* — Young & Thompson

(57) ABSTRACT

There is provided an x-ray detector including a number of adjacent detector modules arranged in a configuration having central parts and peripheral parts. The x-ray detector is configured to have higher dose efficiency in the central parts and lower dose efficiency in the peripheral parts.

12 Claims, 12 Drawing Sheets

(56) References Cited

U.S. PATENT DOCUMENTS

2015/0323685 A1 11/2015 Nelson et al.
2016/0161426 A1 6/2016 Wober
2016/0178762 A1 6/2016 Rodrigues et al.

OTHER PUBLICATIONS

Pack, J., et al., "Investigation of a "Zoom CT" Architecture for Cardiac CT Imaging," The 13th International Meeting on Fully Three-Dimensional Image Reconstruction in Radiology and Nuclear Medicine, 2015, pp. 701-704.
Panetta, D., "Advances in X-Ray Detectors for Clinical and Preclinical Computed Tomography," Nuclear Instruments and Methods in Physics Research, vol. 809, 2016, pp. 2-12.
International Search Report and Written Opinion issued in Application No. PCT/SE2017/050497, dated Aug. 7, 2017.

* cited by examiner

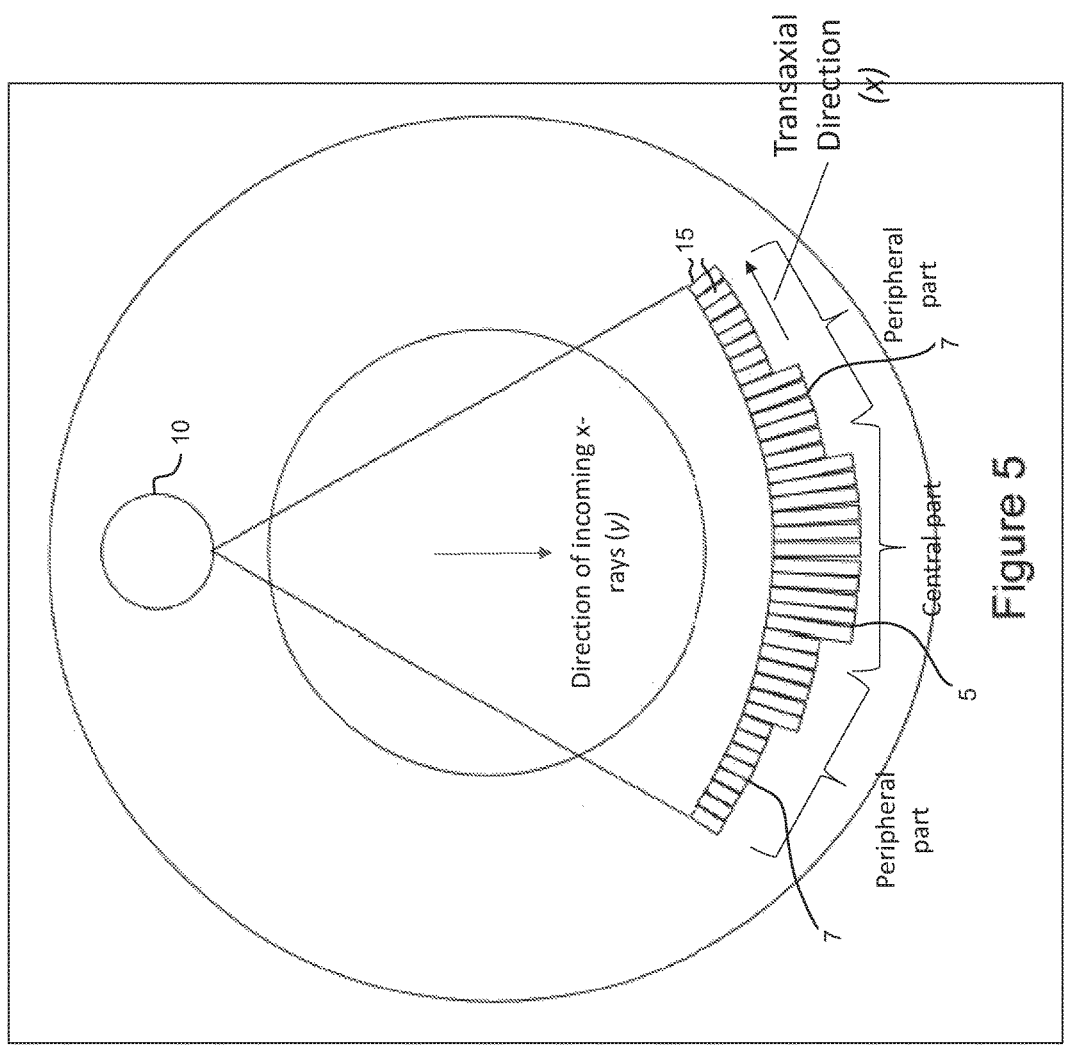

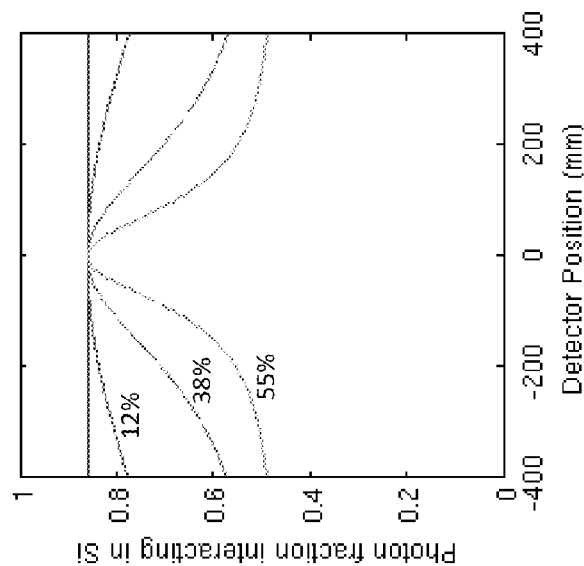
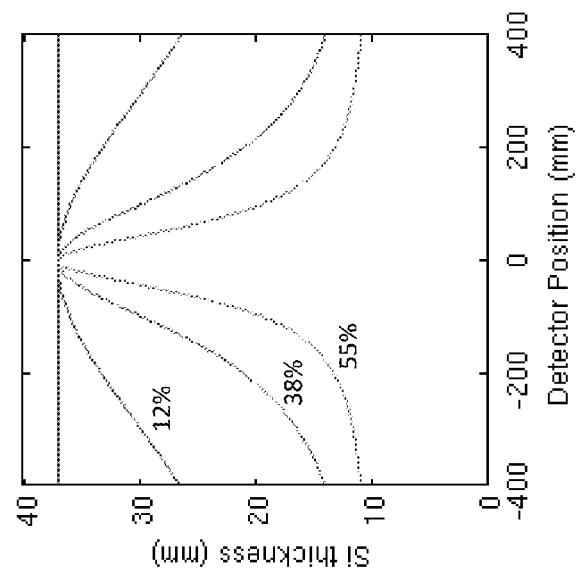
Figure 6B
Figure 6A

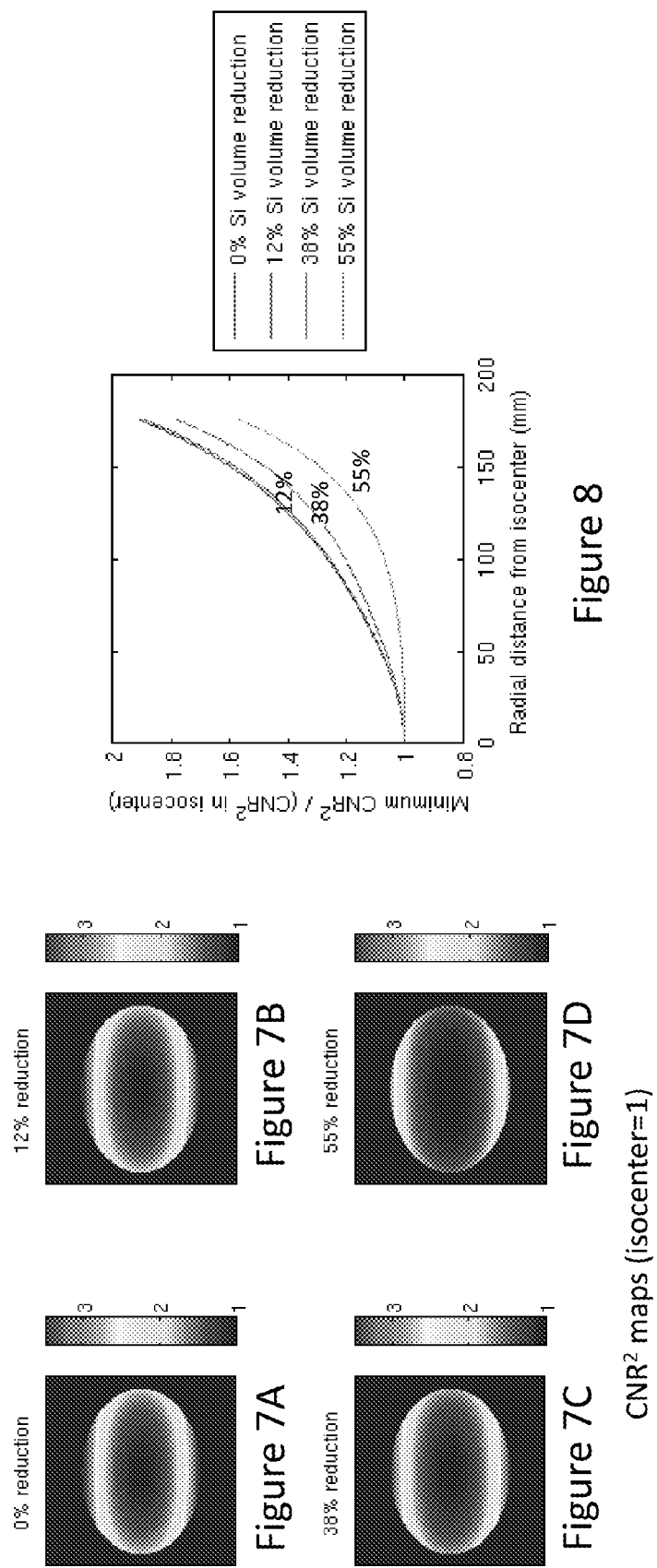

DETECTOR IMPLEMENTATIONS FOR X-RAY DETECTORS

TECHNICAL FIELD

The proposed technology general relates to x-ray imaging, and more particularly to x-ray detectors and x-ray imaging systems.

BACKGROUND

Radiographic imaging such as x-ray imaging has been used for years in medical applications and for non-destructive testing.

Normally, an x-ray imaging system includes an x-ray source and an x-ray detector system. The x-ray source emits x-rays, which pass through a subject or object to be imaged and are then registered by the x-ray detector system. Since some materials absorb a larger fraction of the x-rays than others, an image is formed of the subject or object.

It may be useful to begin with a brief overview of an illustrative overall x-ray imaging system, with reference to FIG. 10. In this non-limiting example, the x-ray imaging system 100 basically comprises an x-ray source 10, an x-ray detector system 20 and an associated image processing device 30. In general, the x-ray detector system 20 is configured for registering radiation from the x-ray source 10 that may have been focused by optional x-ray optics and passed an object or subject or part thereof. The x-ray detector system 20 is connectable to the image processing device 30 via suitable analog processing and read-out electronics (which may be integrated in the x-ray detector system 20) to enable image processing and/or image reconstruction by the image processing device 30.

In any x-ray detector it is important to obtain the maximum dose efficiency for a certain production cost. By way of example, for a next generation of x-ray detectors that are photon counting spectral it has been proposed in U.S. Pat. No. 8,183,535 to use edge-on detectors with Silicon as detector material. If the Silicon is made deeper the absorption of x-rays will increase and thus the dose efficiency increase. However since more Silicon is required to make the detector thicker it also mean the detector will be more expensive to manufacture. This is a general problem with other materials as well, and also with other expensive aspects of the detector implementation.

It is therefore desirable to find effective ways of building an x-ray detector.

SUMMARY

It is an object of the present invention to provide an x-ray detector comprising a number of adjacent detector modules.

It is also an object of the present invention to provide an x-ray imaging system.

These and other objects of the present invention are met by embodiments of the present invention.

According to a first aspect of the proposed technology, there is provided an x-ray detector comprising a number of adjacent detector modules arranged in a configuration having a first group of the detector modules placed in a central part of the configuration and a second group of the detector modules placed in peripheral parts of the configuration on each side of the central part of the configuration, wherein the x-ray detector is configured to have higher dose efficiency in the central part and lower dose efficiency in the peripheral parts.

In this way, a highly cost-efficient modular x-ray detector can be provided.

According to a second aspect, there is provided an x-ray imaging system comprising such an x-ray detector.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which:

FIG. 5 is a schematic diagram illustrating of still another example of modular x-ray detector according to an embodiment of the invention.

FIGS. 6-8 are schematic diagrams illustrating examples of simulations of an elliptical water phantom using the x-ray detectors of FIGS. 1-4.

DETAILED DESCRIPTION

Figure 1:
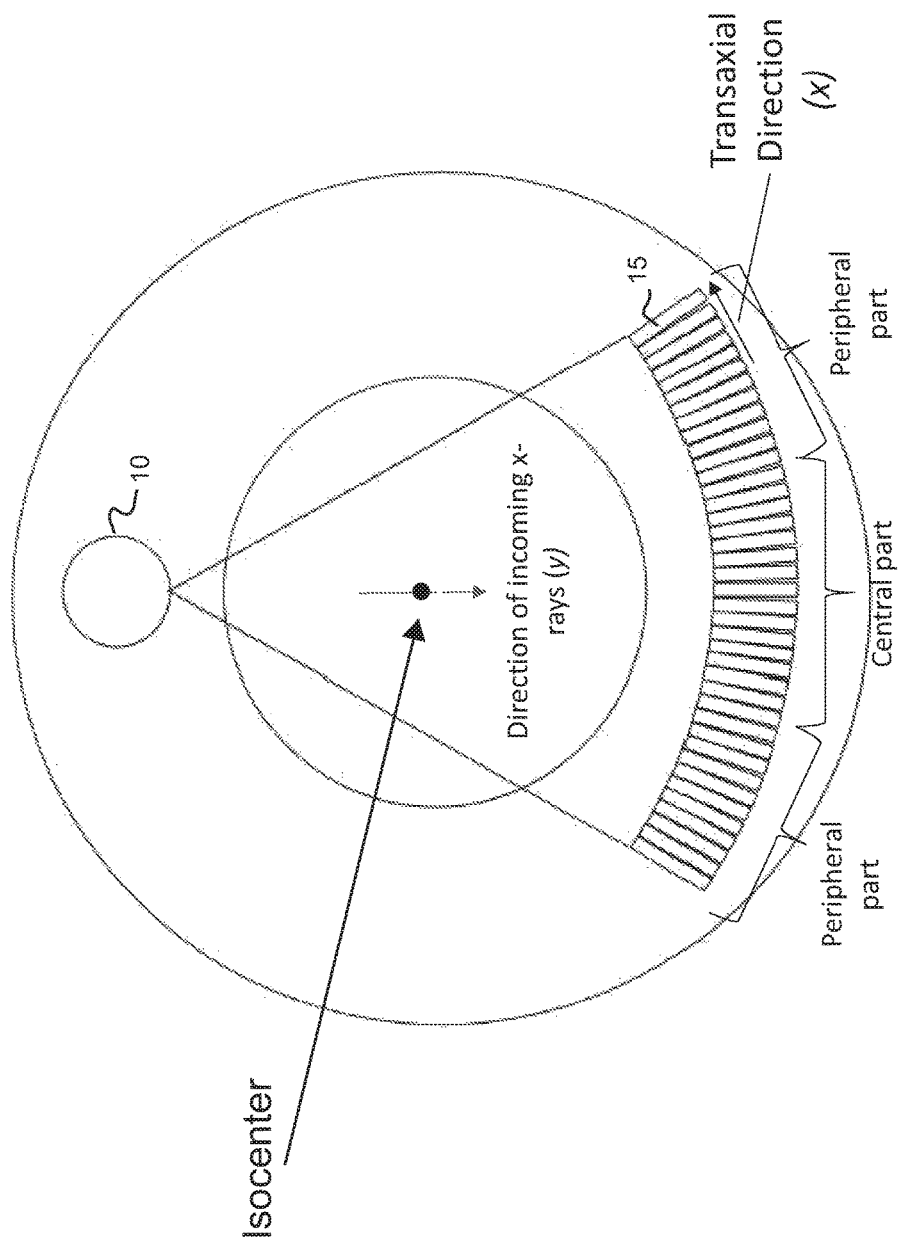
FIG. 1 is a schematic diagram illustrating an example of a conventional modular x-ray detector in a uniform configuration.

In FIG. 1, the detector thickness is uniform across the curved detector which is usually the case for state of the art CT detectors. It is here assumed that the detector is based on a number of adjacent detector modules or parts. The effective detector area may be oriented edge-on to the incoming x-rays.

FIG. 1 illustrates an X-ray source 10, a direction of incoming x-rays (y), the transaxial direction (x), and a configuration of adjacent detector modules 15. The adjacent detector modules 15 are shown in a configuration having a central part 5 and peripheral parts 7 on each side of the central part 5.

FIGS. 2-5 show the configuration of adjacent detector modules 15 with a first group of the detector modules 5 placed in the central part of the configuration, (the first group of detector modules 5 also referred to as central detector modules 5), and a second group of the detector modules 7 placed in the peripheral parts of the configuration on each side of the central part of the configuration, (the second group of detector modules also referred to as peripheral detector modules 7), of the modular x-ray detector.

It should be understood that in the present invention other configurations are also possible, e.g. including a linear geometrical configuration rather than a curved geometrical configuration.

A basic idea in the present invention is to provide an x-ray detector comprising a number of adjacent detector modules 15 arranged in a configuration having a first group of the detector modules 5 placed in a central part of the configuration and a second group of the detector modules 7 placed in peripheral parts of the configuration on each side of the central part of the configuration, wherein the x-ray detector is configured to have higher dose efficiency in the central part and lower dose efficiency in the peripheral parts.

By way of example, the x-ray detector has a material variation along the detector configuration with a larger thickness of detector material in the central part than in the peripheral parts.

As an alternative or a complement, the x-ray detector may have a material variation along the detector configuration with a first type of detector material with higher dose efficiency in the central part and a second type of detector material with lower dose efficiency in the peripheral parts.

For example, the first type of material is Cadmium Telluride (CdTe), Cadmium Zink Telluride (CZT) and/or Gallium Arsenide, and the second type of material is Silicon.

Optionally, the x-ray detector may be configured to have higher spatial resolution in the central part than in the peripheral parts.

As an example, the x-ray detector is configured with smaller pixels in the central part than in the peripheral parts.

In a particular example, the x-ray detector is configured with smaller pixels near the isocenter of the detector.

In an example embodiment, an effective detector area of the x-ray detector is oriented edge-on to the incoming x-rays, and central detector modules are thicker in the direction of incoming x-rays than peripheral detector modules.

For example, the thickness of the detector modules may be varied gradually or varied in one or more steps with at least two different thicknesses.

It is also possible to use a filler material with similar scatter properties as the detector material, wherein the filler material is arranged in the regions with a smaller thickness of detector material.

In this case, the total thickness of the detector and filler material is preferably made constant across the detector to make the scatter distribution more homogeneous.

Optionally, the detector material thickness profile of the x-ray detector is chosen to minimize the maximum variance in a resulting image for a specified total volume of detector material.

In a particular example, the x-ray detector comprises a depth-segmented detector, and a reduced number of depth segments is used in the peripheral parts compared to the central part and/or the length of each depth segment is reduced in the peripheral parts compared to the central part.

By way of example, the adjacent detector modules may be arranged in a curved geometrical configuration.

According to another aspect, there is provided an x-ray imaging system comprising an x-ray detector as described herein.

By way of example, the x-ray imaging system is a Computed Tomography, CT, system.

In a particular example, the x-ray imaging system is configured to apply basis material decomposition to generate an image with the same appearance independently of the detector thickness profile.

Optionally, the x-ray imaging system may be configured to apply iterative reconstruction by using different regularization strength in central and peripheral parts.

The invention will now be described with reference to illustrative, non-limiting examples.

For example, we propose a way to optimize dose efficiency at a minimum cost by varying the detector thickness, with a larger thickness in the center of the overall detector area. It is assumed that the detector has a generally curved geometrical configuration. By way of example, for a modular detector 15, central detector modules 5 are thus thicker in the direction of incoming x-rays than peripheral detector modules 7.

Expressed differently, it is thus proposed to build a detector using thinner detector modules in the peripheral parts than in the central part of the detector.

In other words, less detector material in the detector periphery saves cost.

Figure 9:
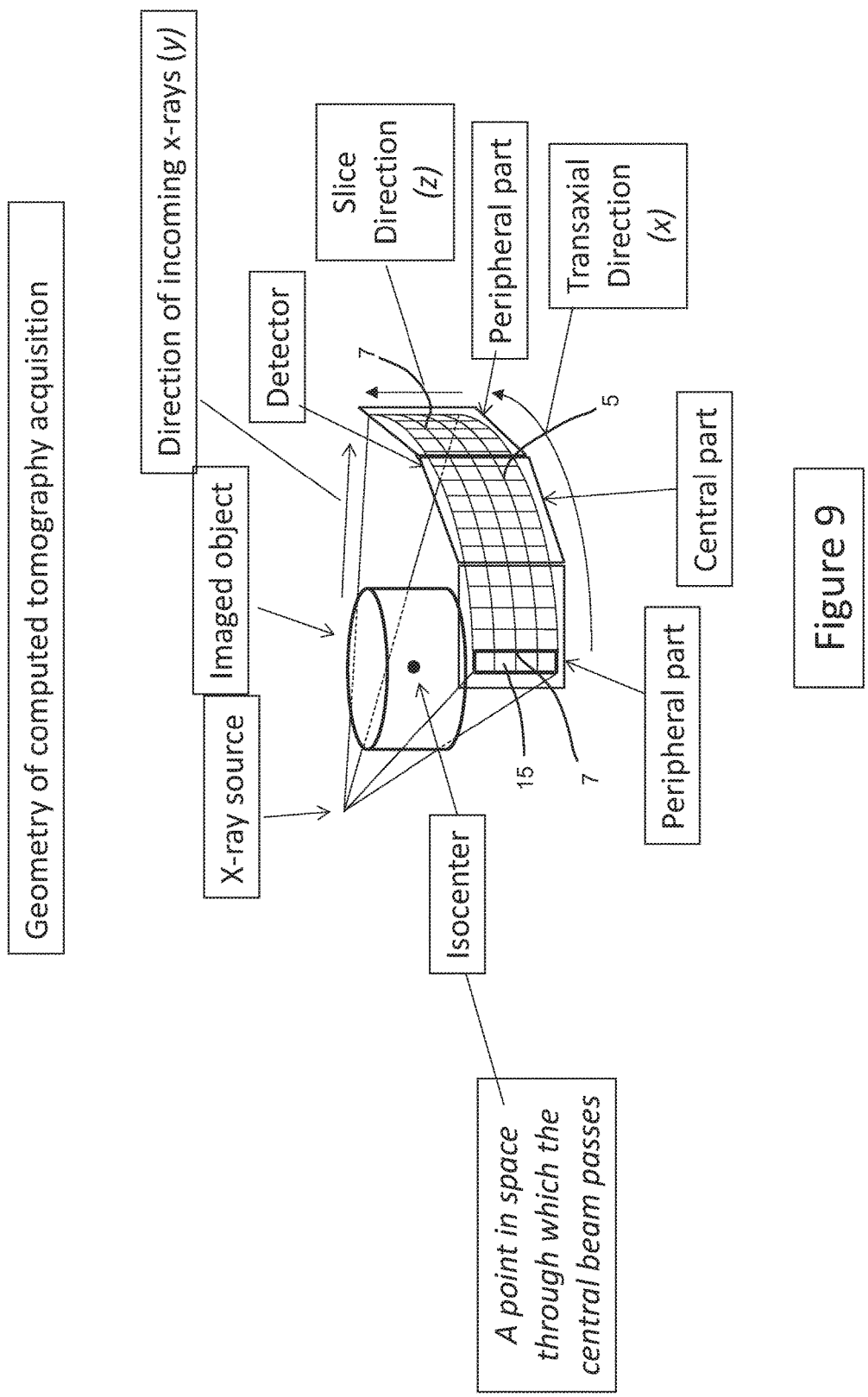
FIG. 9 is a schematic diagram illustrating an example of a configuration for Computed Tomography acquisition.
Figure 10:
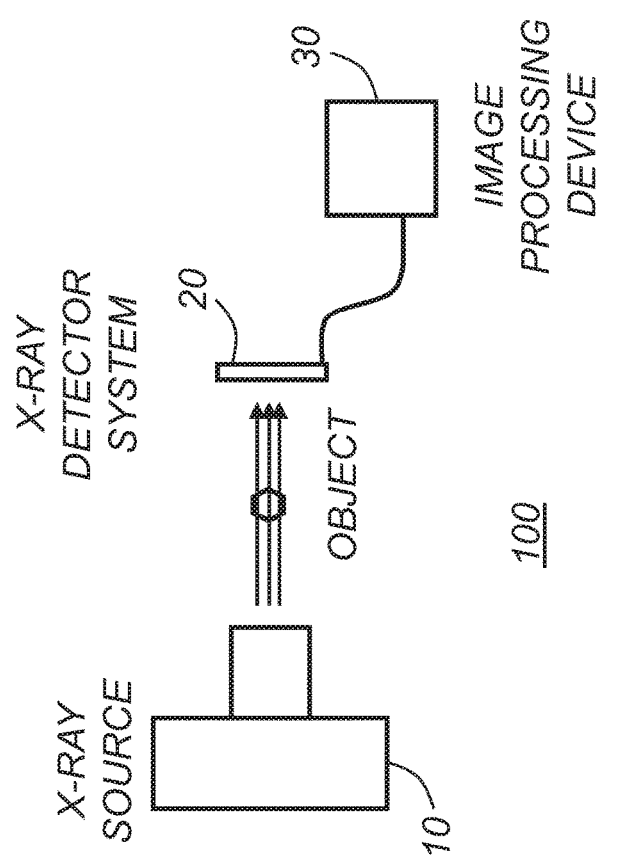
FIG. 10 is a schematic diagram illustrating an example of an overall x-ray imaging system.

FIG. 9 is a schematic diagram illustrating an example of a configuration for Computed Tomography acquisition. Relative to the curved geometrical configuration of the detector, the detector can be seen as consisting of central detector modules 5 at the central part and peripheral detector modules 7 at the peripheral parts located on each side of the central part of the configuration, depending on the position along the detector in the transaxial direction. The central part of the detector comprises the part of the detector that measures rays passing close to the isocenter (center of rotation). The peripheral parts of the detector comprises the parts of the detector that measures rays passing far from the isocenter.

The inventors have recognized that in computed tomography the information value to the image for a certain x-ray hitting the detector will be higher for the x-rays hitting the detector in the center compared to the periphery. This is typically true for all imaging tasks such as the human head or heart. It is also shown by Wang, Xie and Pelc in Proc SPIE 691334-1 that peripheral detector modules or parts will only affect peripheral parts of the resulting image.

Therefore, an idea is to save cost/optimize dose efficiency by varying the (silicon) detector thickness across the detector with a maximum efficiency in the center of the detector since this area has highest impact on dose efficiency.

As indicated in FIGS. 2-5, the thickness can be varied in different ways and/or amounts.

Figure 2:
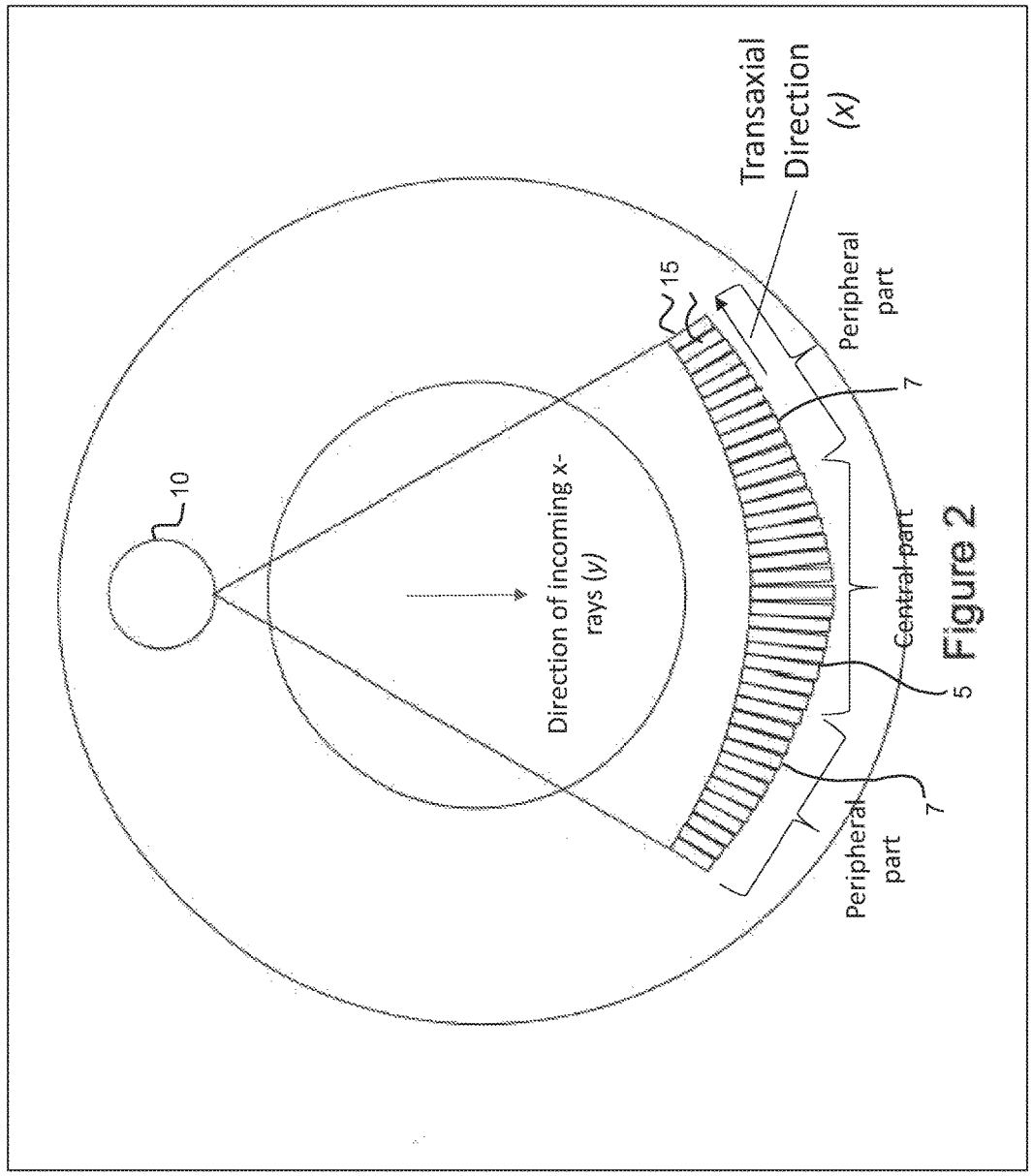
FIG. 2 is a schematic diagram illustrating an example of a modular x-ray detector according to an embodiment of the invention.

FIG. 2 is a schematic diagram illustrating an example with 12% less detector material such as Silicon.

Figure 3:
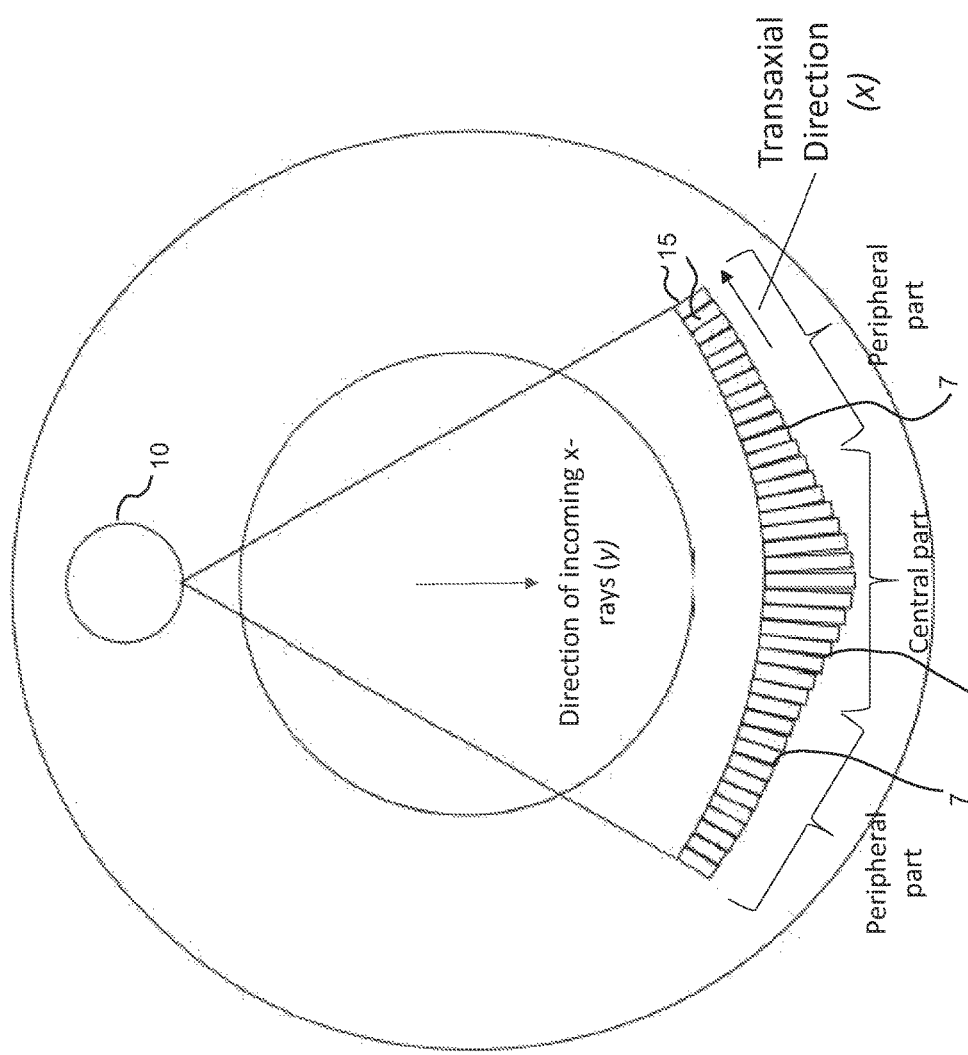
FIG. 3 is a schematic diagram illustrating another example of a modular x-ray detector according to an embodiment of the invention.

FIG. 3 is a schematic diagram illustrating an example with 38% less detector material such as Silicon.

Figure 4:
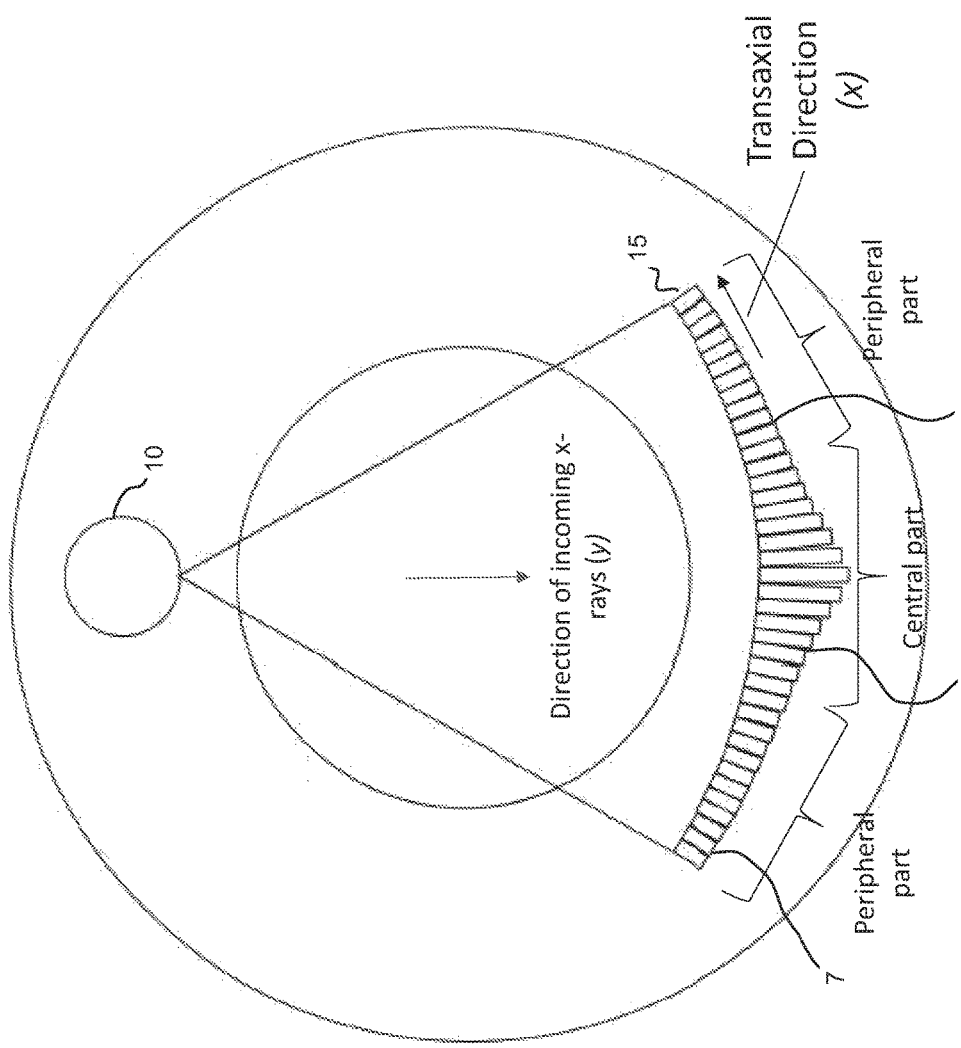
FIG. 4 is a schematic diagram illustrating of yet another example of modular x-ray detector according to an embodiment of the invention.

FIG. 4 is a schematic diagram illustrating an example with 55% less detector material such as Silicon.

FIG. 5 is a schematic diagram illustrating an example of a segmented detector with variation of the thickness or depth in steps.

Examples of the cost in dose efficiency are presented in FIGS. 6-8 showing simulations of an elliptical water phantom.

12% less Silicon with negligible CNR decrease
38% less Silicon with 7% lower minimum $CNR^2$ in peripheral parts
55% less Silicon with no decrease of the global CNR minimum For manufacturing purposes it may be advantageous to vary the thickness in steps, as indicated in FIG. 5. It could be only one step (two different thicknesses) or it can be any larger number of steps.

By way of example, the detector material thickness profile may be chosen to minimize the maximum variance in the image for a specified total volume of detector material.

Figure 13:
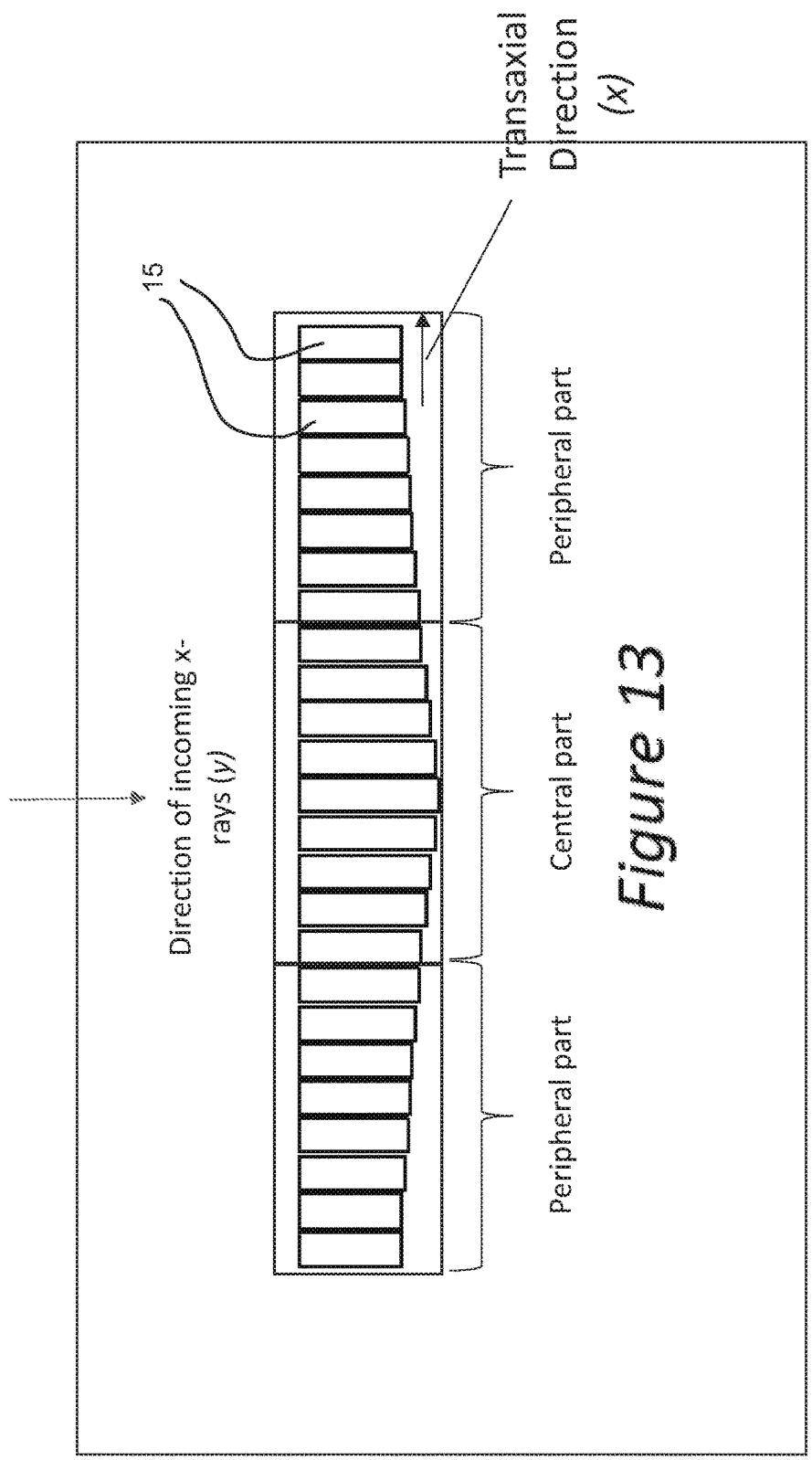
FIG. 13 is a schematic diagram illustrating an example of a modular x-ray detector with detector modules arranged in a generally linear geometrical configuration according to an embodiment of the invention.

FIG. 13 is a schematic diagram illustrating an example of a modular x-ray detector with detector modules arranged in a generally linear geometrical configuration according to an embodiment of the invention.

It is also possible to apply basis material decomposition to generate an image with the same appearance independently of the detector thickness profile.

Figure 11:
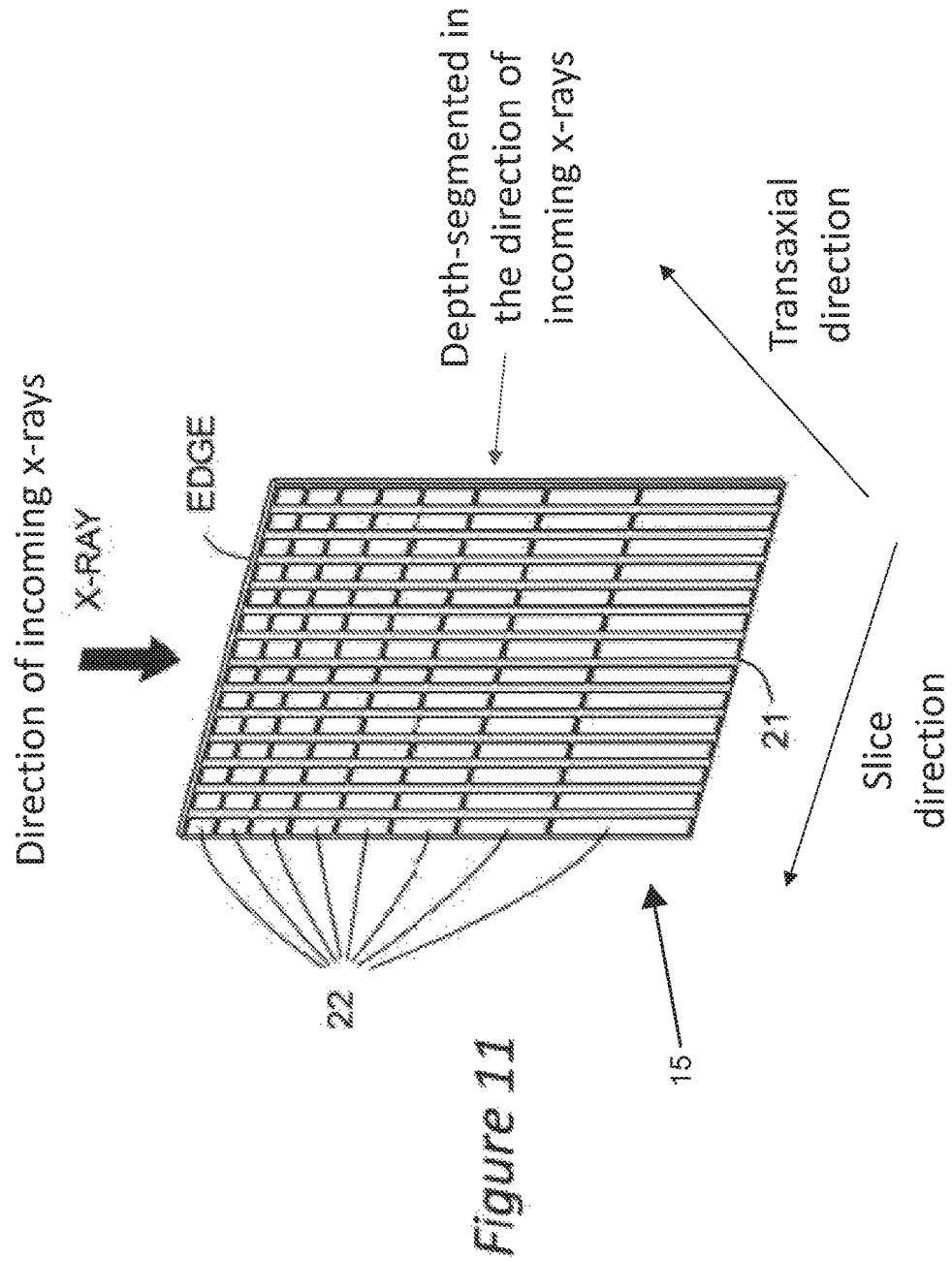
FIG. 11 is a schematic diagram illustrating an example of detector module according to an exemplary embodiment.

FIG. 11 is a schematic diagram illustrating an example of detector module according to an exemplary embodiment. In this example, the x-ray sensitive part 21 of the detector module 15 is split into so-called depth segments 22 in the depth direction, again assuming the x-rays enter through the edge.

Normally, a detector element is an individual x-ray sensitive sub-element of the detector. In general, the photon interaction takes place in a detector element and the thus generated charge is collected by the corresponding electrode of the detector element.

Each detector element typically measures the incident x-ray flux as a sequence of frames. A frame is the measured data during a specified time interval, called frame time.

Depending on the detector topology, a detector element may correspond to a pixel, especially when the detector is a flat-panel detector. A depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode.

The detector strips of a depth-segmented detector normally correspond to the pixels of an ordinary flat-panel detector. However, it is also possible to regard a depth-segmented detector as a three-dimensional pixel array, where each pixel (sometimes referred to as a voxel) corresponds to an individual depth segment/detector element.

In case the implementation comprises a depth-segmented detector, it is possible to use a reduced number of depth segments in the periphery in order to minimize power consumption and data rate.

Alternatively, one may reduce the length of each depth segment in order to reduce pileup and input capacitance in each readout channel.

To avoid artifacts generated from the inhomogeneous distribution of scatter in the detector at the transition between regions with different detector thicknesses, one may use a cheap filler material with similar scatter properties as the detector material to fill in the regions with a smaller thickness of the detector material. By making the total thickness of the detector and filler material constant across the detector, the scatter distribution is made more homogeneous.

Some examples of possible practical considerations:
In practice, a small number (2-5) different sensor thicknesses may be used.
It is important to avoid artifacts at the locations where the sensor thickness changes.
When using basis material decomposition, the difference in effective spectral response can be compensated for, to get a seamless image appearance.
If the unequal amount of detector scatter gives artifacts where the sensor thickness changes, a filler material may be inserted instead of the removed silicon to equalize the scatter distribution.
No sharp increase in noise will be seen in the image since the effect of the lower quantum efficiency sets in gradually with increasing distance from isocenter.
In some situations, the noise in the peripheral regions may become higher than in the central part. If this is disturbing to the eye, it can be countered with iterative reconstruction by using different regularization strength in central and peripheral parts.

In general, the noise variance in the reconstructed image is dominated by the noise contribution from the most noisy x-ray projection rays, which are often the ones passing near the isocenter, where the path length through the object is largest. Furthermore, the noise in the measurements made by the central part of the detector contributes to the noise in the entire reconstructed image, whereas the noise in the measurements made by the peripheral parts of the detector only contributes to the noise in the peripheral parts of the reconstructed image. It is therefore important to have as high detection efficiency as possible in the central part of the detector, at a reasonable cost.

This can generally be accomplished by material variation along the curved detector configuration, as proposed herein.

Since it is expensive to manufacture a detector with high dose efficiency, one may therefore choose to manufacture a detector with higher dose efficiency in the central part and a lower dose efficiency in the peripheral parts. One way of achieving this is to make the detector material thicker in the central part and thinner in the periphery. Another way is to use a first, type of detector material (with higher dose efficiency) in the central part and a second type of detector material (with lower dose efficiency) in the peripheral parts.

Typically a more expensive detector material may thus be used for the central part that has higher performance, for example an exotic expensive material and the peripheral parts may be made in a less exotic material such as Silicon that is cheaper. By way of example, a more expensive detector material in the center could be CdTe or CZT (Cadmium Zink Telluride) or another possible material is Gallium Arsenide.

Since the most interesting image features are often located near the isocenter, it is also important to have the highest spatial resolution in the central part of the image, as discussed in *Investigation of a "zoom CT" architecture for cardiac CT imaging*, by Jed Pack, Ge Wang, Jiao Wang, Bruno De Man, and Jeffrey Carr of GE Global Research, at The 13th International Meeting on Fully Three-Dimensional Image Reconstruction in Radiology and Nuclear Medicine, Newport, R.I., USA 2015.

This can be achieved by having smaller pixels near the isocenter. Smaller pixels adds most information to the image if they are at the center of the detector for most imaging tasks. Smaller pixels is a driver of data rate and power and normally there is a constraint on total power and data rate that a detector can handle in order to be practical. Too much power would put the detector at too high temperature or mean the temperature in ambient room will be uncomfortably high or it will require expensive cooling system installations such as water cooling instead of air cooling. There is a maximum amount of data that can be sent through the slip rings and the image often needs to be displayed fast, to use small pixels only for central part of the detector will help the trade-off.

It is thus possible to vary the spatial resolution in such a way that the spatial resolution in the center is higher than in the periphery, since small pixels is a driver of cost and it is more optimum to have smaller pixels in the center of the detector and not as is the state of the art today uniform pixel size across the detector. The proposed technology therefore suggest building a detector with a set of smaller pixels in a central part of the detector compared to more peripheral parts of the detector.

It will be appreciated that the techniques and devices described herein can be combined and re-arranged in a variety of ways.

For example, specific functions such as image processing tasks may be implemented in hardware, or in software for execution by suitable processing circuitry, or a combination thereof.

The steps, functions, procedures, modules and/or blocks described herein may be implemented in hardware using any conventional technology, such as semiconductor technology, discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

Figure 12:
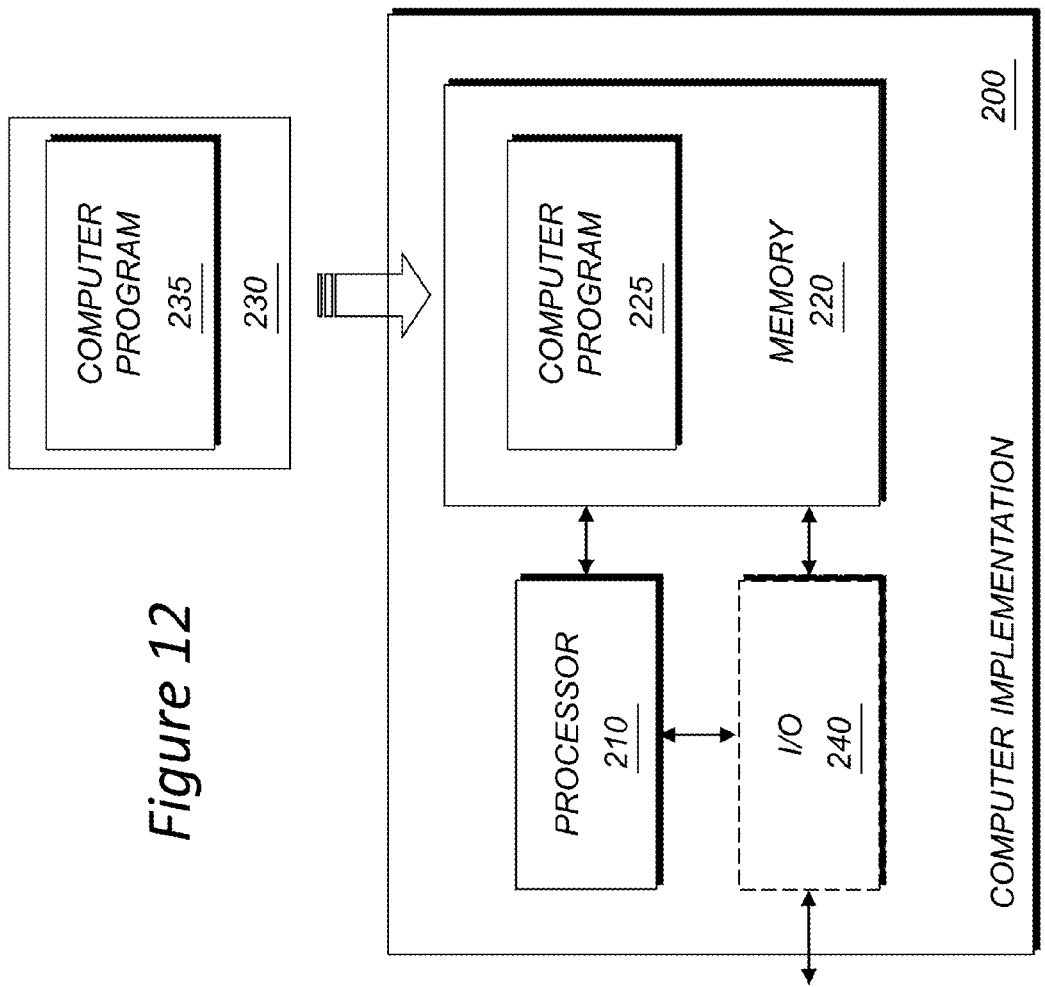
FIG. 12 is a schematic diagram illustrating an example of a computer implementation according to an embodiment.

FIG. 12 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. By way of example, it will be appreciated that the arrangements described herein can be implemented, combined and re-arranged in a variety of ways. In particular, different part solutions in the different embodiments can be combined in other configurations, where technically possible.

The invention claimed is:

1. A modular x-ray detector for Computed Tomography (CT) acquisition, said modular x-ray detector comprising:
   plural adjacent detector modules,
   wherein said modular x-ray detector is configured for detecting incoming x-rays, and said detector modules are arranged in a configuration having a first group of the detector modules placed in a central part of the configuration, also referred to as central detector modules, and a second group of the detector modules placed in peripheral parts of the configuration on each side of the central part of the configuration, also referred to as peripheral detector modules, of the modular x-ray detector, with respect to an isocenter of the x-ray detector and in a transaxial direction of the modular x-ray detector,
   wherein the central detector modules are arranged for measuring x-rays passing closer to the isocenter than the peripheral detector modules, and
   wherein the modular x-ray detector has a higher dose efficiency in the central detector modules placed in the central part and a lower dose efficiency in the peripheral detector modules placed in the peripheral parts according to at least one of the following structural configurations:
   i) the modular x-ray detector has a larger thickness, in a direction of the incoming x-rays, of detector material in the central detector modules placed in the central part than in the peripheral detector modules placed in the peripheral parts,
   ii) the modular x-ray detector has a first type of detector material with higher dose efficiency in the central detector modules placed in the central part and a second type of detector material with lower dose efficiency in the peripheral detector modules placed in the peripheral parts, and
   iii) the modular x-ray detector comprises a depth-segmented detector, which is segmented in the direction of the incoming x-rays, wherein a reduced number of depth segments is used in the peripheral detector modules placed in the peripheral parts compared to the central detector modules placed in the central part and/or a length of each depth segment is reduced in the peripheral detector modules placed in the peripheral parts compared to the central detector modules placed in the central part.

2. The modular x-ray detector of claim 1, wherein the first type of material is Cadmium Telluride (CdTe), Cadmium Zink Telluride (CZT) and/or Gallium Arsenide, and the second type of material is Silicon.

3. The modular x-ray detector of claim 1, wherein an effective detector area of the x-ray detector is oriented edge-on to the incoming x-rays, and central detector modules are thicker in the direction of incoming x-rays than peripheral detector modules.

4. The modular x-ray detector of claim 3, wherein the thickness of the detector modules in the direction of the incoming x-rays is varied gradually or varied in one or more steps with at least two different thicknesses in a direction of the incoming x-rays.

5. The modular x-ray detector of claim 1, wherein a filler material is arranged in the peripheral detector modules having a smaller thickness of detector material in a direction of the incoming x-rays than the central detector modules, and the detector material of the peripheral detector modules has given scatter properties and the filler material same scatter properties as the detector material.

6. The modular x-ray detector of claim 5, wherein the thickness of the modular x-ray detector and filler material in a direction of the incoming x-rays is constant across the central and peripheral detector modules of the modular x-ray detector by arranging the filler material in the peripheral detector modules.

7. The modular x-ray detector of claim 1, wherein a detector material thickness profile of the modular x-ray detector in a direction of the incoming x-rays is chosen to minimize a maximum variance in a resulting image for a volume of detector material.

8. The modular x-ray detector of claim 1, wherein the adjacent detector modules are arranged in a curved geometrical configuration.

9. An x-ray imaging system comprising the modular x-ray detector of claim 1.

10. The x-ray imaging system of claim 9, wherein the x-ray imaging system is a Computed Tomography, CT, system.

11. The x-ray imaging system of claim 9, wherein the x-ray imaging system comprises a processing circuitry configured to apply a basis material decomposition to generate an image with a same appearance independently of a detector thickness profile in a direction of the incoming x-rays.

12. The x-ray imaging system of claim 9, wherein the x-ray imaging system comprises a processing circuitry configured to apply an iterative reconstruction by using a first regularization strength for the central detector modules placed in the central part and a second, different regularization strength for the peripheral detector modules placed in the peripheral parts.

* * * * *